United States Patent
Amano

(10) Patent No.: US 7,154,096 B2
(45) Date of Patent: Dec. 26, 2006

(54) DIAGNOSTIC IMAGING DEVICE FOR MEDICAL USE

(75) Inventor: Masaharu Amano, Ibaraki (JP)

(73) Assignee: Shimadzu Corporation, Kyoto-Fu (JP)

( * ) Notice: Subject to any disclaimer, the term of this patent is extended or adjusted under 35 U.S.C. 154(b) by 321 days.

(21) Appl. No.: 10/942,481

(22) Filed: Sep. 16, 2004

(65) Prior Publication Data

US 2005/0082487 A1    Apr. 21, 2005

(30) Foreign Application Priority Data

Oct. 17, 2003   (JP) ............................. 2003-358014

(51) Int. Cl.
*G01T 1/164* (2006.01)
*A61B 5/05* (2006.01)
*A61B 6/00* (2006.01)

(52) U.S. Cl. ........................... 250/363.03; 250/363.04; 378/4; 378/21; 378/209

(58) Field of Classification Search ........... 250/363.03, 250/363.04; 378/4, 21, 209; 600/411, 431, 600/436

See application file for complete search history.

(56) References Cited

U.S. PATENT DOCUMENTS

| | | | |
|---|---|---|---|
| 6,449,331 B1 * | 9/2002 | Nutt et al. ..................... 378/19 |
| 6,490,476 B1 * | 12/2002 | Townsend et al. ........... 600/427 |
| 6,631,284 B1 * | 10/2003 | Nutt et al. .................... 600/427 |
| 6,661,866 B1 * | 12/2003 | Limkeman et al. ............ 378/19 |
| 2003/0206609 A1 * | 11/2003 | Kling et al. .................... 378/4 |

\* cited by examiner

*Primary Examiner*—David Porta
*Assistant Examiner*—Mark R. Gaworecki
(74) *Attorney, Agent, or Firm*—Darby & Darby

(57) ABSTRACT

A diagnostic imaging device is provided to detect cancers in early stages with a high degree of accuracy while minimizing the risk of X-ray exposure that can be caused by the X-ray CT examination, taking advantage of the PET examination which provides a means of efficient early detection of cancers while minimizing the risk of radiation exposure. A PET gantry 20 and a CT gantry 30 are arranged sequentially relative to a common examination table 10, a control unit provided in a console 40 controlling the examination table 10, the PET gantry 20, and the CT gantry 30, and an examination subject 13 laid on a top board 11 of the examination table 10 is inserted into a tunnel 21 of the PET gantry 20 for collecting PET data in order to reconstruct a PET image, display the PET image on an image monitor provided in the console 40, allow a doctor to make a determination as to whether the examination subject 13 should be further subjected to a CT examination by sending it into a tunnel 31 of the CT gantry 30, and allow necessary actions to be taken in accordance with the determination.

5 Claims, 2 Drawing Sheets

DIAGNOSTIC IMAGING DEVICE FOR MEDICAL USE

INCORPORATION BY REFERENCE

The present application claims priority under 35 U.S.C. §119 to Japanese Patent Application No. 2003-358014 filed on Oct. 17, 2003. The content of the application is incorporated herein by reference in its entirety.

FIELD OF THE INVENTION

The invention relates to a diagnostic imaging device for medical use, in particular, a diagnostic imaging device for medical use suitable for early detection of cancers.

DESCRIPTION OF THE RELATED ART

It is extremely important to detect cancers in early stages for their treatments. Among various kinds of methods and devices known for early detections of cancers, Positron Emission Tomography (PET) examination is considered one of the most promising methods because it can detect cancerous cells while they are quite small and does not cause any radiation exposure problem.

The PET examination detects a distribution image (cross-sectional image) of positron emitting nuclides on a particular cross section of an examination subject. A drug with positron emitting nuclides that is attracted to cancerous lesions can be administered into the subject's body. Since two gamma rays are emitted 180° apart when a positron decays, the simultaneous incidents of those gamma rays can be detected by monitoring for them 360° around the body. Since a nuclide exists on a line connecting those incident locations, the data of the line that connect those incident locations is obtained as the location data. A distribution image of nuclides can thus be reconstructed by collecting these location data for a specified period of time and then applying an mathematical operation to the data. Since this distribution image (cross-sectional image) identifies the size and shape of a cancerous legion itself, a direct diagnosis can be made.

On the other hand, since this PET image shows only the accumulation or distribution of the nuclide and does not indicate where it exists in the human body tissue. Therefore, it has been customary to conduct X-ray CT examination for providing images of the distribution of X-ray absorption coefficient as a means of identifying body tissues to make a more solid diagnosis in combination of the PET images with the CT images. However, the examination using an X-ray CT device causes a problem of exposing the examination subject to X-rays.

Moreover, although a system has been disclosed in Laid open patent application H7-20245 (patent document 1) in which a common examination table is used for a PET device and an X-ray CT device, such a system uses data obtained from the X-ray CT device for the absorption compensation of the PET data, and does not obtain CT images from the X-ray CT device for diagnostic purposes.

The present invention provides a medical diagnostic imaging device for detecting cancers in early stages with a high degree of accuracy while minimizing risks of X-ray exposure from X-ray CT examination. The present invention takes advantage of PET, which can detect cancers at their early stages while minimizing risks of radiation exposure.

The invention also provides a medical diagnostic imaging device for automating the process of diagnosis, supporting doctors' judgments, and further facilitating doctors' work.

SUMMARY OF THE INVENTION

To achieve the intended object, a diagnostic imaging device for medical use according to the present invention is equipped with: a PET data collection unit and a CT data collection unit arranged in tandem; an examination table for a common usage of said two data collection units having a bed top board for examining a subject; a PET image reconstruction unit for reconstructing PET images from the collected PET data; a CT image reconstruction unit for reconstructing CT images from the collected CT data; and a control unit for first controlling said PET data collection unit and PET image reconstruction unit to collect PET data and to reconstruct PET images for an examination region of the examination subject, displaying the obtained PET images as well as prompting the user for an input indicating whether to advance to CT data collection and CT image reconstruction processes or not, and then controlling said examination table, CT data collection unit and CT image reconstruction unit either to execute or not to execute the CT data collection and the CT image reconstruction for the same region depending on the input result.

Moreover, said control unit can control said PET data collection unit and PET image reconstruction unit to collect PET data and reconstruct PET images for an examination region of the examination subject, display the obtained PET images as well as make a determination whether any pixel value that exceeds a specified threshold value exists in said image, prompt the user for an input indicating whether to advance to CT data collection and CT image reconstruction processes or not if it determines that there exists such a pixel value, and then control said examination table, CT data collection unit and CT image reconstruction unit either to execute or not to execute the CT data collection and the CT image reconstruction for the same region depending on the input result.

The control device controls the PET data collection unit and PET image reconstruction unit to collect PET data and reconstruct PET images for an examination region of the examination subject and displays the obtained PET images, and then prompts the doctor to enter an input indicating whether to advance to CT data collection and CT image reconstruction processes or not. The doctor can enter either an instruction to advance to CT data collection and CT image reconstruction if the doctor judges that there is an indication of possible cancer, or an instruction not to advance to CT scanning if the doctor judges that there is no indication of cancer upon observation of the displayed PET images. Because the PET scanning and PET image displays are done first and then the doctor who has seen the images is prompted to enter a decision whether to advance to CT scanning, the doctor is able to concentrate on the diagnosis of cancer by means of the PET images and is helped on the decision process of whether to advance to the next step of CT examination. The whole process is made easier for the doctor, who can order CT scanning only when there is a suspicion for cancer. This avoids the risk of unnecessary exposure to X-rays while taking advantage of the PET examination which provides an efficient means to detect cancer early.

If the control device can further make a determination as to whether the pixel values of the PET images obtained from the preliminary PET scanning exceeds a specified threshold value, this may help the doctor in making a close observation of the PET images to see if there are any regions where cancers can be suspected, supporting the doctor's diagnosis and making the job of early detection of cancers easier, safer and more secure.

PREFERABLE EMBODIMENTS OF THE INVENTION

The diagnostic imaging device for medical use according to the present invention is described below with reference to the accompanying drawings.

Embodiment 1

Figure 1:
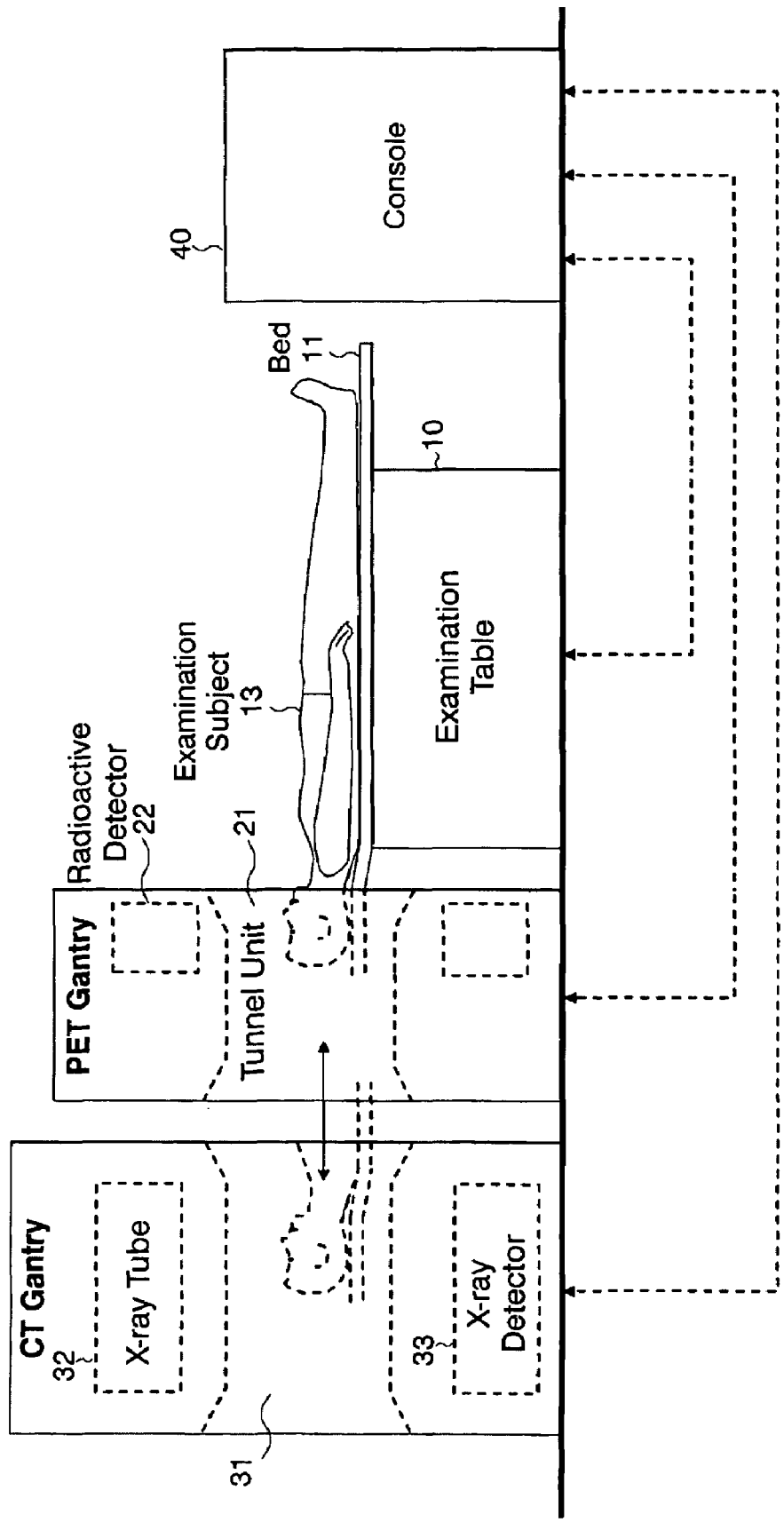
FIG. 1 is a block diagram showing an embodiment of the invention.

As shown in FIG. 1, the diagnostic imaging device for medical use according to this invention comprises an examination table 10, a PET gantry 20, a CT gantry 30, and a console 40. The PET gantry 20 constitutes the PET data collection unit, having a tunnel unit 21 in the center and radiation detectors 22 arranged like a ring around the tunnel unit 21. An examination subject 13 administered with a radio active drug is inserted into the tunnel unit 21, and the radiation detectors 22 arranged like a ring around it detects radiations released from the radiating drug existing in the examination subject 13. Two gamma rays released from a positron emitting nuclide at a time in 180° directions opposite to each other are detected as they enter simultaneously into two diametrically apart radiation detectors 22, which are arranged like a ring, and the detected data are collected in such a way that the presence of the radioactive drug is detected on the line connecting the two radiation detectors 22.

The CT gantry 30 constitutes the X-ray CT data collection unit, having a tunnel unit 31 in the center and a rotating mechanism (not shown) surrounding the tunnel unit 31 to rotate an X-ray tube 32 and an X-ray detector 33. The X-ray detector 33 is a one dimensional detector of a specified length, or a combination of a plurality of them arranged in multiple layers, and the X-ray scanning is performed for cross sections of the examination subject 13 inserted in the tunnel unit 31 by rotating the X-ray detector 33 and the X-ray tuber 32, so that X-ray absorption distribution data can be collected.

The examination table 10 is designed in such a way that it can be commonly used for the PET gantry 20 and the CT gantry 30. The PET gantry 20 and the CT gantry 30 are arranged relative to the examination table 10 in the order of gantries 20 and 30, so that the examination subject 13 placed on the bed top board 11 can be inserted into their tunnel portions 21 and 31. The console 40 comprises, in addition to a control unit for controlling the abovementioned examination table 10, PET gantry 20 and CT gantry 30, input devices such as a keyboard and a mouse as well as an image monitoring device. The console 40 also contains the PET image reconstruction unit and the CT image reconstruction unit.

Figure 2:
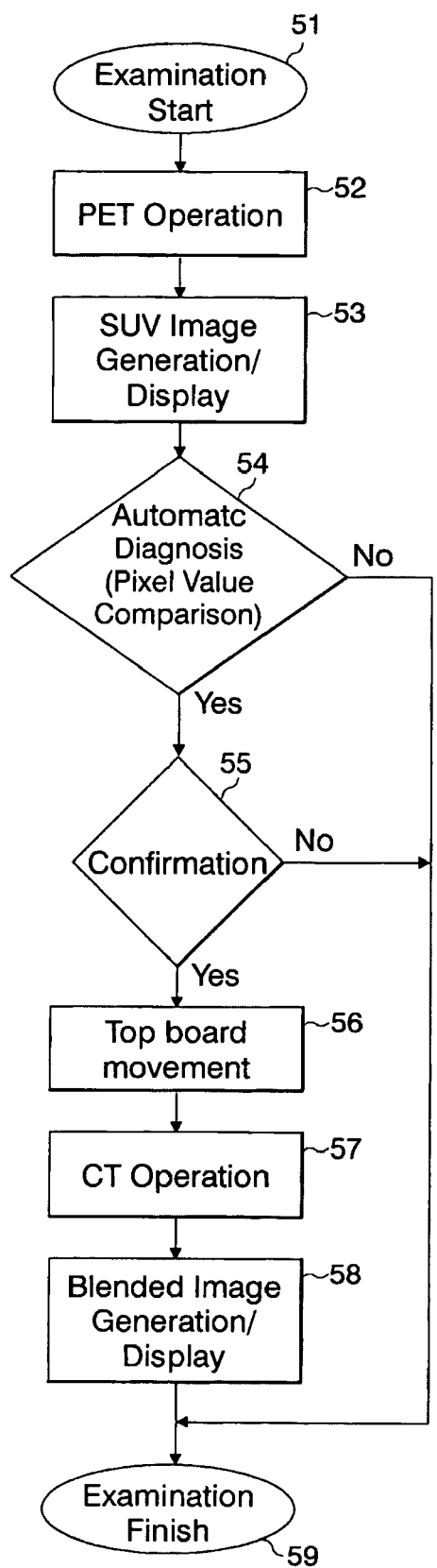
FIG. 2 is a flow chart for describing the operating principle of the embodiment.

When an instruction for starting the examination is entered by operating the keyboard of the console 40, the control unit starts the examination as shown in the flow chart of FIG. 2 (step 51), the PET data collection unit executes the PET data collection, and the PET image reconstruction unit executes the image reconstruction process (step 52). At this point, the examination subject 13 has been administered with a drug marked with a positron emitting nuclide such as FDG for 40 to 60 minutes, so that it is in a condition where this drug is accumulated around its cancerous legions. The examination subject 13 is laid on the bed top board 11 of the examination table 10. The examination table 10 is controlled by the control unit to move, and the entire body (or a particular examination region if the examination region is limited in advance) of the examination subject 13 is scanned.

When the PET image of each cross section of the entire body of the examination subject 13 is reconstructed, a SUV image is prepared for each cross section, which will then be displayed (step 53). This SUV is an index value that indicates cancer and has a correspondence relation with the pixel value of the PET image. The SUV image is an image having this SUV as the pixel value. This SUV image can be generated by the control unit or by the PET image reconstruction unit.

Next, the control unit performs an automatic diagnosis based on this SUV image (step 54). This is done by comparing the pixel value of the SUV image with a specified threshold value, determining that the region is highly suspected of cancer if there is any part where the pixel value exceeds the threshold value, clearly marking the region with colors, and displaying such messages as "Cancer is suspected," "Advance to CT scan," "Yes," and "No." If no region exceeds the threshold value, the program advances to step 59 to terminate the examination.

If there is any region that exceeds the threshold value, it prompts the doctor for an input to advance to the CT scan by means of the abovementioned image and message displays (step 55). Observing the SUV image displayed on the screen, the doctor can make a judgment as to whether to advance to CT examination or not, and clicks either "Yes" or "No" on the screen using a mouse, or enters his or her decision by operating switches provided on the console 40. If "No" (Do not advance to CT examination) is entered, it advances to step 59 to terminate the examination.

If "Yes" (Advance to CT examination) is entered, the control unit controls the examination table 10 to move the top board 11, and causes the examination subject 13 to enter the tunnel unit 31 of the CT gantry 30 (step 56). The control unit controls the CT data collection unit and the CT image reconstruction unit to cause them to perform CT data collection and CT image reconstruction on the subject 13 (step 57). Although CT data collection and image reconstruction can be performed for the entire body of the subject 13, but it is more preferable to restrict it to a vicinity of the area where the abovementioned SUV is high, from the standpoint of minimizing X-ray exposure. Such a CT examination control can be automatically done by the control unit based on the SUV image.

Once the CT image is obtained in this manner, a combined image produced by overlaying the CT image with the PET image at the control unit is displayed to finish the examination (step 59). The doctor can do a more precise diagnosis by closely observing this combined image.

Although the PET gantry 20 and the CT gantry 30 are arranged in that order relative to the examination table 10 in the above description, they can be arranged in the opposite order, and they don't have to be built into each enclosure separately, but rather can be built into a single gantry wherein both the PET data collection unit and the CT data collection unit are contained in a single enclosure. Also, although it was described in the above that the PET image reconstructing unit and the CT image reconstructing unit are enclosed in the console 40, they can be constructed separately, and the separately constructed PET device and CT device can be connected in the control unit.

Moreover, although the SUV image is generated to support the doctor's judgment, it is also possible to display the reconstructed PET image and a message prompting the doctor to enter a decision whether to advance to the CT examination or not upon observing the image, and to skip the process of generating an SUV image. In such a case, only the PET image itself is displayed without identifying the areas with high SUV by color coding. The doctor would have to identify the areas suspected to be cancerous from the PET images without the support offered by the SUV images, but this should not pose a problem as the doctor becomes more experienced in this method.

Furthermore, although only PET data collection is described, the system may also simultaneously collect transmission data for absorption compensation in order to obtain a more accurate PET image compensated for absorption, based on said data.

The probability of finding cancer during any general medical checkup is said to be about 2–3%, and the probability of finding cancer improves if the PET examination and the CT examination are done in combination over a case where the PET examination and the CT examination are done independently. On the other hand, it is preferable for a healthy person who has no suspicion of cancer to avoid X-ray exposure, which is unavoidable with the CT examination, as much as possible, so that the invention is meaningful in that it realizes a diagnostic imaging device that can contribute to early detections of cancers while minimizing the risks of X-ray exposure. Hence obvious changes may be made in the specific embodiment of the invention described herein, such modifications being within the spirit and scope of the invention claimed, it is indicated that all matter contained herein is intended as an illustrative and not as limiting in scope.

What is claimed is:

1. A diagnostic imaging device for medical use comprising:
    a PET data collection unit and a CT data collection unit arranged in tandem;
    an examination table for a common usage of said two data collection units having a bed top board for examining a subject;
    a PET image reconstruction unit for reconstructing PET images from the collected PET data;
    a CT image reconstruction unit for reconstructing CT images from the collected CT data; and
    a control unit for controlling said PET data collection unit and PET image reconstruction unit to collect PET data and to reconstruct PET images for a region of the subject, displaying PET images reconstructed from the PET data, prompting a user for an input indicating whether to advance to CT data collection and CT image reconstruction processes or not, and then controlling said examination table, CT data collection unit and CT image reconstruction unit either to execute or not to execute the CT data collection and the CT image reconstruction for the same region depending on the input result.

2. A diagnostic imaging device for medical use of claim 1, wherein said control unit is configured to control said PET data collection unit and PET image reconstruction unit to collect PET data and reconstruct PET images for an examination region of the examination subject, displaying the obtained PET images as well as making a determination whether any pixel value that exceeds a specified threshold value exists in said image, prompt the user for an input indicating whether to advance to CT data collection and CT image reconstruction processes or not if it determines that there exists such a pixel value, and then control said examination table, CT data collection unit and CT image reconstruction unit either to execute or not to execute the CT data collection and the CT image reconstruction for the same region depending on the input result.

3. A diagnostic imaging device comprising:
    a PET data collection unit for collecting PET data;
    a CT data collection unit for collecting CT data, said CT data collection unit disposed next to the PET data collection unit;
    an examination table for carrying a subject commonly to the PET data collection unit and the CT data collection unit;
    a PET image reconstruction unit for reconstructing one or more PET images from the PET data transmitted from the PET data collection unit;
    a CT image reconstruction unit for reconstructing one or more CT images from the collected CT data; and
    a control unit for controlling said PET data collection unit and PET image reconstructing unit, displaying one or more PET images reconstructed from the PET data, prompting for an input to advance to the CT data collection unit, and controlling based on the input entered, said examination table, said CT data collection unit and said CT image reconstruction unit to collect CT data and to reconstruct one or more CT images from the CT data.

4. The diagnostic imaging device for medical use of claim 3, wherein said control unit determines whether any pixel value in any of the PET images exceeds a specified threshold value, and if the pixel value exceeds the specified threshold value, the control unit prompts for an input to advance to the CT data collection unit to collect CT data.

5. The diagnostic imaging device for medical use of claim 3, wherein if said control unit determines that there exists a pixel value that exceeds a specified threshold value and if the input value indicates to the control to advance the table to the CT data collection unit, control controls said examination table, CT data collection unit and CT image reconstruction unit either to execute CT data collection and CT image reconstruction.

* * * * *